(12) United States Patent
Kaplan

(10) Patent No.: US 11,602,576 B1
(45) Date of Patent: Mar. 14, 2023

(54) AIR/GAS COMPRESSOR WITH VIRAL/BACTERIAL ULTRAVIOLET RADIATION FILTRATION

(71) Applicant: Gardner Denver, Inc., Davidson, NC (US)

(72) Inventor: Lawrence Kaplan, Miami Lakes, FL (US)

(73) Assignee: Gardner Denver, Inc., Davidson, NC (US)

(*) Notice: Subject to any disclaimer, the term of this patent is extended or adjusted under 35 U.S.C. 154(b) by 0 days.

(21) Appl. No.: 17/389,993

(22) Filed: Jul. 30, 2021

Related U.S. Application Data

(60) Provisional application No. 63/060,377, filed on Aug. 3, 2020.

(51) Int. Cl.
*A61L 9/20* (2006.01)
*F04B 39/16* (2006.01)

(52) U.S. Cl.
CPC .............. *A61L 9/20* (2013.01); *F04B 39/16* (2013.01); *A61L 2209/111* (2013.01); *A61L 2209/14* (2013.01)

(58) Field of Classification Search
CPC .. A61L 9/20; A61L 2209/111; A61L 2209/14; A61L 2/20; A61L 2/10; A61L 2/24; A61L 2202/25; A61L 2202/14; A61L 2202/16; A61L 9/12; A61L 9/046; A61L 2209/12; A61L 2209/212; A61L 9/205; A61L 9/16; F04B 39/16; F21V 7/0075; F21V 14/025; F21V 21/26; F21V 21/15; F21Y 2115/10; B01D 53/007; B01D 53/869; B01D 53/8675; B01D 53/96; B01D 46/0028; B01D 46/0038; B01D 46/006; B01D 53/8678; B01D 2279/50; B01D 2255/802; B01D 2255/9032; B01D 2257/106; B01D 2257/90; B01D 2257/91; B01D 2251/104; B01D 2258/06; A61M 11/06; A61M 16/10; A61M 16/105; A61M 16/06; A61M 16/0057; A61M 16/0672; A61M 2209/10; A61M 2210/0618; A61M 2205/053; A61M 2202/0208; A61M 2210/0625; A61M 16/101;
(Continued)

(56) References Cited

U.S. PATENT DOCUMENTS

| | | | | |
|---|---|---|---|---|
| 7,151,264 B2* | 12/2006 | Ehlers, Sr. | ........... | B01D 53/007 250/373 |
| 2006/0177356 A1* | 8/2006 | Miller | ............... | A61M 11/06 422/121 |
| 2007/0275651 A1* | 11/2007 | Palmer | ............... | F24F 11/77 454/238 |

* cited by examiner

*Primary Examiner* — Xiuyu Tai
(74) *Attorney, Agent, or Firm* — Advent, LLP; Kevin E. West

(57) ABSTRACT

A breathing air compressor having an inlet air ultraviolet C light radiation emitter and viral and bacterial filtration system for air introduced into the air compressor. The viral and bacterial filtration system includes a cylindrical housing that includes a UVC radiation emitter mounted in a flow-through UVC radiation chamber, an inlet air particulate filter, and a flowmeter for measuring the volume and rate of flow of air to destroy viruses and bacteria present in any air flowing through the UVC chamber that is input air to an air compressor. The air compressor is typically used for generating breathing air for persons such as firemen and SCUBA divers. A controller and monitor unit is connected to the UVC radiation emitter and the flowmeter to shut down the air compressor to prevent air starvation.

4 Claims, 1 Drawing Sheet

(58) Field of Classification Search
CPC ...... A61M 2205/3334; A61M 16/0066; A61M 16/0063; A61M 2016/0033; A61M 2205/3368; A61M 2205/3606; A61M 16/0808; F24F 8/192; F24F 2011/0004; F24F 8/22; Y02A 50/20
See application file for complete search history.

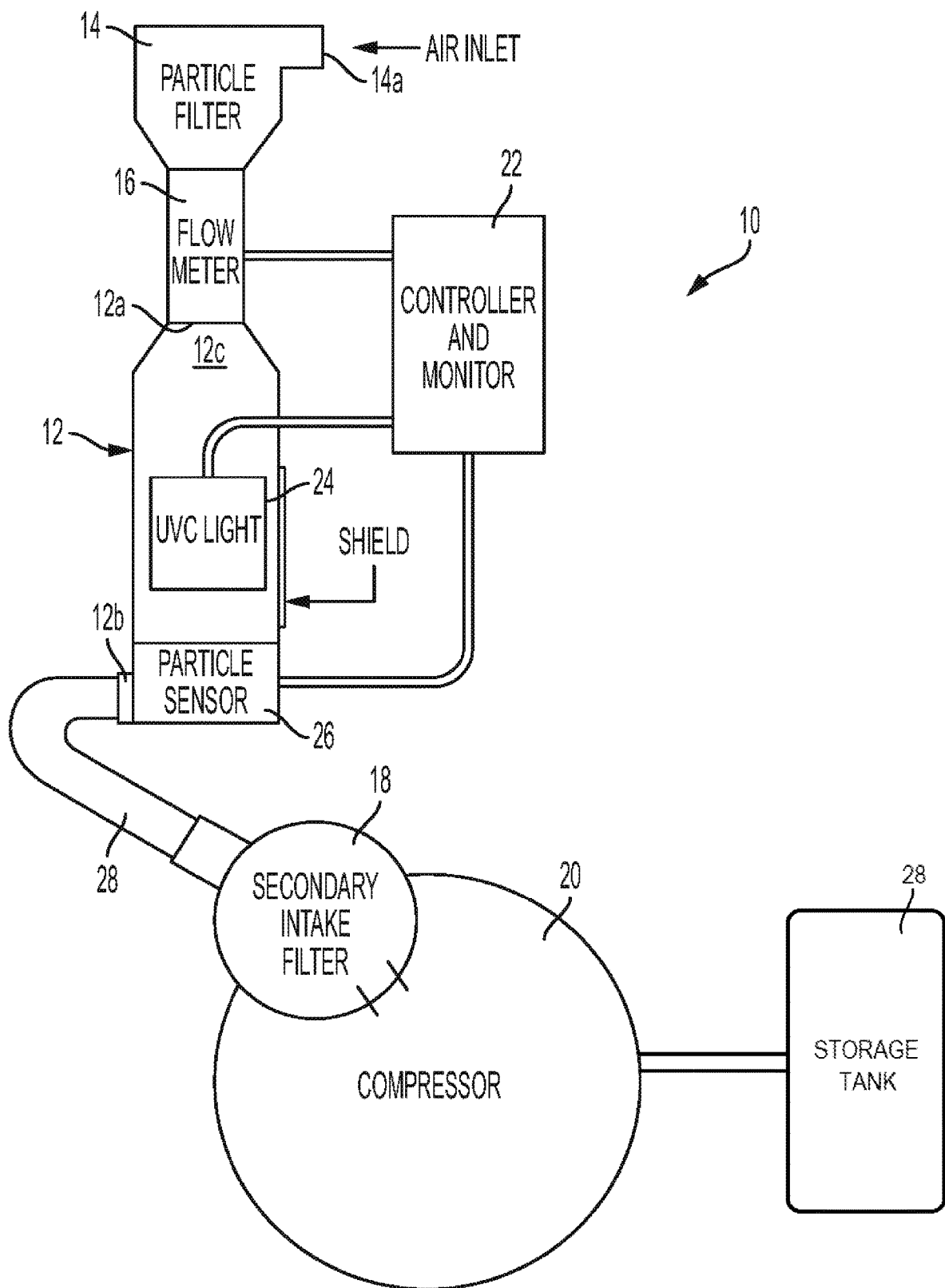

AIR/GAS COMPRESSOR WITH VIRAL/BACTERIAL ULTRAVIOLET RADIATION FILTRATION

CROSS REFERENCE TO RELATED APPLICATIONS

This application claims benefit of U.S. Provisional Patent Application Ser. No. 63/060,377, filed on Aug. 3, 2020.

BACKGROUND OF THE INVENTION

1. Field of the Invention

This invention relates generally to a viral/bacterial ultraviolet radiation (UV) filtration system for purifying inlet air/gas provided to an air/gas compressor, typically used for generating breathing air, and specifically to a UV radiation emitted air/gas filter that can destroy viral and bacterial materials that provided to the ambient air intake of an air/gas compressor that is used typically to generate and store breathing air for human beings.

2. Description of Related Art

Commercial and governmental agencies and businesses use ambient air compressors to provide breathing air for different groups of people, the breathing air being stored in portable air tanks for consumers to breathe. Examples would be breathing air provided to firemen and policemen and SCUBA divers. Also breathing air is provided for medical use in hospitals for patients who need to receive increased breathing air under pressure.

It is essential that the breathing air produced from an air compressor and stored in a tank, such as a pressurized air tank, be safe for human consumption including that the air/gas does not contain any bacteria or viral organisms that could endanger the health of a human being. It is well-known that bacteria and viruses can produce very serious illnesses in human beings and produce diseases that are also very contagious to others, once obtained by a human being.

Ultraviolet radiation or ultraviolet light is effective in laboratory studies for killing bacteria on computer screens, toothbrushes, and other objects. It has also been shown to affect viruses in similar ways that it affects bacteria. Ultraviolet radiation is lethal to bacteria and viruses because of its high frequency that scrambles and damages viral and bacterial nuclear material. When the DNA or RNA of a virus or bacteria is damaged, often lethal mutations are triggered that also prevent a virus or bacteria from reproducing properly. Applicant has prepared an air/gas ultraviolet radiation filter for use with an air compressor for breathing air that can remove viruses and bacteria from the ambient air taken into the air compressor to prevent humans from receiving air compressor breathing air that contains viruses or bacteria, resulting in a viral and bacterial contaminants filtration using ultraviolet light.

SUMMARY OF THE INVENTION

A viral/bacterial ultraviolet (UV) radiation air/gas filtration system including a cylindrical housing for attachment to the air inlet conduit for an air compressor that produces breathing air for human personnel. The rigid housing comprises an air/gas flow-through ultraviolet radiation chamber, a flow-through UV chamber inlet opening at one end, and a flow-through UV chamber outlet exhaust opening at the opposite end. An ultraviolet radiation emitter is centrally located along a central axis of the flow-through UV radiation chamber, the purpose being to radiate, with ultraviolet energy, air that flows through the UV radiation chamber to destroy viruses and bacteria present in the air. The exterior surface of the housing and walls of the UV radiation chamber can include an ultraviolet radiation shield to protect surrounding people from any ultraviolet radiation from the filtration system.

A particulate air filter is positioned across the primary air inlet to the housing that supplies air to the air compressor, to remove particles from air entering the air in the intake of the flow-through UV radiation chamber. The particulate air filter can also filter micro-organisms such as bacteria, viruses, molds, and spores using an ultrahigh mechanical filter in addition to the bacterial and viral filtration provided by UV light.

An air volume flowmeter is placed in a housing inlet passage that is connected to the outlet of the air inlet particle filter, so that the volume amount and flow rate, of air flowing through the UV radiation chamber to the air compressor, can be measured to prevent air starvation to the air compressor. Sensors associated with a flowmeter can communicate to an onboard computer connected to the controller and monitor, to manage flow rates of the airflow and dwell times of the airflow in the UV radiation chamber. Alerts, such as emergency alerts, can also be generated from the controller and monitor to communicate with a computer to alert cell phones and cloud-based websites of the appropriate personnel to ensure that the system functions properly and the air compressor is not starved for air.

The housing exhaust end of the UV radiation chamber can also include a particle sensor of the air output from the UV radiation chamber that has already been treated with ultraviolet radiation for destruction of viral and bacterial material. An outlet air exhaust conduit from the UV chamber is connected to the particle sensor and also to a secondary intake filter that is attached to the inlet of the air compressor that will be used to generate compressed air for breathing.

The flowmeter is electrically connected to a controller and monitor unit to assist in monitoring airflow dwell time exposure to UV radiation and to help monitor airflow volume and rate through the flowmeter, and outlet flow air volume to prevent the air compressor from being starved of air. It is important to ensure that there is proper airflow through the UV radiation chamber. If there is not sufficient air for the compressor, starving the air compressor, the controller and monitor unit can actuate an alarm and the air compressor can be turned off. The controller and monitor unit can also monitor UV radiation levels of the UV radiation emitter.

Using the invention described herein, an air compressor can be used to generate viral and bacteria-free breathing air or gases for safety testing to ensure the air compressor is working properly.

The controller and monitor unit for the airflow volume and rate and UV radiation monitor can be connected to the Internet as well as smart phones that allow monitoring of airflow to calculate dwell time of the air passing by the UV radiation light. The dwell time is crucial in providing enough time for the ultraviolet radiation to destroy the bacteria and viruses passing through the air UV radiation chamber. The UV radiation emitter can also be monitored so that the UV light intensity radiation can be adjusted to provide more or less energy for destroying viruses and bacteria located inside the UV radiation chamber.

The system could also include an air compressor speed control to synchronize UV radiation amount and time to air volume passing through the UV chamber so that the air compressor does not become starved for air and the air is sanitized of bacteria and viruses.

The controller and monitor unit can also send data and air compressor activity alerts to a website or to a cloud-based website for the air compressor operators or their clients and their service center. A relay can be provided that can turn off the compressor when necessary.

It is believed that the flow rate and volume of air and the time of UV light and radiation are key to destroying viruses and bacteria passing through the UV radiation chamber.

It is an object of this invention to provide a viral and bacterial air filtration system for an air compressor that produces breathing air for human beings to make the breathing air received from the air compressor safe.

BRIEF DESCRIPTION OF THE DRAWING

FIG. 1 shows a schematic drawing of one embodiment of the invention described herein.

PREFERRED EMBODIMENT OF THE INVENTION

Referring now to FIG. 1, the viral/bacterial filtration system 10 is shown comprising a rigid, cylindrical, housing 12 and flow-through UV radiation chamber 12c, having an upper air passage inlet 12a connected to an air inlet particle filter 14, that has an inlet opening 14a to receive inlet ambient air that is supplied to air compressor 20. The housing outlet of particle filter 14 is connected to a passage containing air flowmeter 16 that can measure the volume and flow rate of air (or gas) flowing from particle filter 14 into the UV radiation chamber 12c. Particle filter 14 can filter microorganisms such as bacteria, viruses, molds, and spores using an ultrahigh mechanical filter in conjunction with ultraviolet light.

The UV radiation chamber 12c includes an exhaust outlet 12b connected to a secondary intake filter 18. Compressor 20, used for generating breathing air, typically provides air to a storage tank 28 that can be used for people requiring breathing air such as firemen, policemen, and SCUBA divers.

An ultraviolet radiation emitter 24, mounted along a central axis inside flow-through UV radiation chamber 12c, is used to emit ultraviolet radiation to destroy viruses and bacteria within the air within the chamber 12c, while the air flows through from air inlet 14a into compressor 20. The UV radiation emitter 24 is monitored by controller and monitor 22 in terms of the intensity of the UV radiation. Controller and monitor 22 also controls flowmeter 16 and the rate of flow of air permitted into compressor 20. Controller and monitor 22 also can sense particles from particulate sensor 26 that, if necessary, can shut down the air compressor 20. UVC light from UV radiation emitter 24 has a wavelength of 200 nm-280 nm, useful for disinfection.

UV radiation emitter 24 can also have an intensity sensor to monitor UV radiation, to be increased or decreased, as provided by controller and monitor unit 22. Another important variable is airflow dwell time of receiving UV radiation that can be controlled with data from the flow meter 16. Controller and monitor 22 monitors air volume to the compressor that can also help prevent starvation of air to compressor 20.

In operation, when the air compressor 20 is turned on, the air compressor 20 creates lower air pressure in the UV radiation chamber 12c, creating inlet airflow and airflow into the secondary intake filter 18. Ambient air under higher pressure enters air inlet 14a and flows through the flow meter. With the UV radiation emitter 24 turned on, by the controller and monitor 22, air can flow through particulate filter 14 and through the flowmeter 16 which measures the volume and rate of flow of air into and through flow-through UV radiation chamber 12c. The air molecules inside flow-through chamber 12 are radiated by UV radiation emitter 24, destroying virus and bacteria contained in the air flowing there through. Note that any solid unwanted particles can be removed through particle filter 14. Also, a secondary intake filter 18 can detect particles before they enter into compressor 20.

The controller and monitor unit 22 is responsible for ensuring the volume of air flowing through the system to the compressor is sufficient to prevent air starvation to the air compressor 20. The system can provide an alarm to a smartphone or computer and the Internet to provide data and information to interested parties including the compressor user and certified quality organizations monitoring the quality of breathing air produced by the compressor 20. An alarm can be provided that requires compressor 20 to be shut down and the UV radiation emitter 24 to be shut off, due to any improprieties in the air flowing through the system for the volume of air provided. The controller and monitor unit 22 can have two-way communication to an onboard computer to manage flow rates of the airflow and dwell times of the airflow, and also communicate alerts to cell phones or cloud accounts of concerned parties as to the condition of the system.

In summary, the purpose of the viral and bacterial UV radiation filtration system is to provide virial and bacteria-free air to an air compressor 20 that generates breathing air. The system also prevents stray UV radiation from being emitted out of the filtration housing with a shield, to protect people working with the compressor. The system also includes a particulate filter for any particles that might be received into the air inlet and a particulate sensor to shut the system off if unwanted particles are present in the inlet air to the compressor.

The controller and monitor 22 (and the entire system) can be in communication with a computer through Wi-Fi or ethernet cable that allows data, concerning the quality of air output from the compressor 20, to be transmitted to the air compressor user or certified air monitor organization for quality breathing air specialists, who monitor the quality of breathing air produced. The data produced can be put on a website that is cloud-based for access by all interested parties affected by the quality of air or gases produced by the compressor. The data can also be provided to third-party smartphones that include alarms to the equipment.

The breathing air compressor viral and bacterial filtration system and method are shown and described herein in what is considered to be the most practical and preferred embodiment. It is recognized, however, that departures may be made therefrom within the scope of the invention and that obvious modifications will occur to a person skilled in the art.

What I claim is:

1. An air filtering system configured to remove bacteria and viruses from ambient air and supply bacteria and virus-free breathing air for a storage tank comprising:

a housing having a first end and a second end, said first end fluidly connected to a particle filter configured to remove air particles from entering the housing; said housing having:

an ultraviolet C light (UVC) radiation chamber, an inlet opening at one end of said UVC radiation chamber, an exhaust opening at the opposite end of the UVC radiation chamber, and a UVC radiation emitter located along a central axis of said UVC radiation chamber to radiate with ultraviolet energy air that flows through the UVC radiation chamber to damage and remove bacteria and viruses present that flow through the UV radiation chamber;

a controller in communication with the UVC chamber, wherein the controller monitors the intensity of the radiation emitted by the UVC radiation emitter; and an air compressor fluidly connected to the housing, wherein the air compressor is configured to create a lower air pressure in the UVC radiation chamber, draw the ambient air into the air filtering system and provide the breathing air to the storage tank, wherein, the controller is configured to provide a computer data regarding air compressor activity and air quality output via Wi-Fi communications.

2. The air filtering system as in claim 1, including:

said housing having an exterior surface and an ultraviolet radiation shield mounted on said housing exterior surface to protect people surrounding said housing from UVC radiation.

3. The air filtering system as in claim 1, including:

a flowmeter having a flowmeter air inlet connected to the particle filter air outlet and a flowmeter air outlet connected to said UVC radiation chamber inlet opening wherein the flowmeter measures the volume and the flow rate of the air flowing from the particle filter into the UVC radiation chamber.

4. The air filtering system as in claim 1, including:

a secondary intake particle filter fluidly connected between the UVC radiation chamber and the air compressor, wherein the secondary intake particle filter filters remaining particles in the airflow prior to entering the compressor.

\* \* \* \* \*